United States Patent [19]

Ozawa et al.

[11] 4,310,682

[45] Jan. 12, 1982

[54] HALO-SALICYLANILIDE

[76] Inventors: Isao Ozawa, No. 255-31, Takahata, Fujishima, Komaki, Aichi Prefecture; Tomiyoshi Ito, No. 35-9-1, Hara-cho, Suita, Osaka Prefecture; Yoshiki Hamada, No. 5-5-3, Wagogaoka, Togo-cho, Aichi-gun, Aichi Prefecture; Isao Takeuchi, No. 15-5-2, Asahidai, Owariasahi, Aichi Prefecture, all of Japan

[21] Appl. No.: 123,655

[22] Filed: Feb. 22, 1980

[30] Foreign Application Priority Data

Feb. 28, 1979 [JP] Japan ................................ 54-23800

[51] Int. Cl.$^3$ .......................................... C07C 103/76
[52] U.S. Cl. .................................... 560/142; 564/179
[58] Field of Search .................. 260/559 S; 560/142, 560/143; 564/179

[56] References Cited

U.S. PATENT DOCUMENTS

| | | | |
|---|---|---|---|
| 2,703,332 | 3/1955 | Bindler et al. | 260/559 S |
| 2,802,029 | 8/1957 | Schuler | 260/559 S |
| 3,079,297 | 2/1963 | Schraufstatter et al. | 260/559 S X |
| 3,113,067 | 12/1963 | Strufe et al. | 260/559 S X |
| 3,147,300 | 9/1964 | Schraufstatter et al. | 260/559 S X |
| 3,332,996 | 7/1967 | Zerweck et al. | 260/559 S |
| 3,839,443 | 10/1974 | Meek | 260/559 S |
| 3,906,023 | 9/1975 | Büchel et al. | 260/559 S X |
| 3,906,034 | 9/1975 | Franz et al. | 260/559 S X |
| 3,927,071 | 12/1975 | Forsyth et al. | 260/559 S X |
| 3,989,826 | 11/1976 | Forsyth et al. | 260/559 S X |

FOREIGN PATENT DOCUMENTS

| | | | |
|---|---|---|---|
| 589376 | 3/1959 | Italy | 260/559 S |
| 45-28157 | 5/1970 | Japan | 260/559 S |
| 50-197512 | 12/1975 | Japan | 260/559 S |

Primary Examiner—Arthur P. Demers
Attorney, Agent, or Firm—Cooper, Dunham, Clark, Griffin & Moran

[57] ABSTRACT

A halo-salycylanilide of the following formula

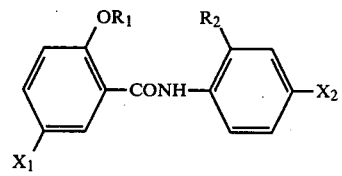

wherein $R_1$ represents hydrogen or acyl group, $R_2$ represents alkyl group, and both $X_1$ and $X_2$ represent halogen, has high antifungal and bactericidal activity.

6 Claims, 2 Drawing Figures

HALO-SALICYLANILIDE

BACKGROUND OF THE INVENTION

1. Field of the Invention

The invention relates to a halo-salicylanilides having high antifungal and bactericidal activity.

More particularly, the invention relates to a halo-salicylanilide of the following formula

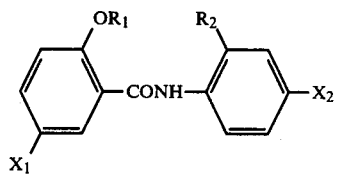

wherein $R_1$ represents hydrogen or acyl group, $R_2$ represents alkyl group, and both $X_1$ and $X_2$ represent halogen.

2. Description of the Prior Art

Hitherto some kinds of halo-salicylanilides are provided as compounds having antifungal and bactericidal activity.

For instance, U.S. Pat. No. 2,703,332 provided a halo-salicylanilide of the following formula

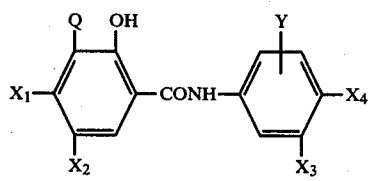

wherein Q represents a member selected from the group consisting of hydrogen, chlorine, bromine and iodine, $X_1$ and $X_2$ each represent a member selected from the group consisting of hydrogen, chlorine, bromine, iodine and $CH_3$, $X_3$ represents a member selected from the group consisting of hydrogen, chlorine, bromine and $CF_3$, and $X_4$ and Y each represent a member selected from the group consisting of hydrogen, chlorine and bromine.

U.S. Pat. No. 2,802,029 provided a halo-salicylanilide of the following formula

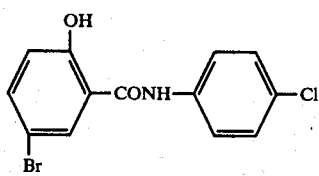

French Pat. No. 2,162,454 provided a halo-salicylanilide of the following formula

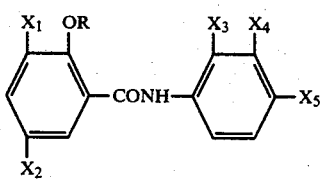

wherein R represents hydrogen or acyl group, both $X_1$ and $X_2$ represent bromine or iodine, and $X_3$, $X_4$, $X_5$ and $X_6$ each represent hydrogen or halogen having an atomic number less than 53, and ACTA PHARMACEUTIA SINICA, Vol. X, No. 11, Nov., 1963, Shanghai, provided a halo-salicylanilide of the following formula

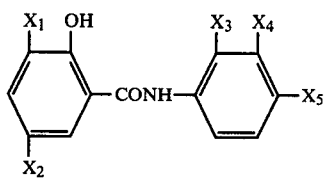

wherein $X_1$ and $X_2$ each represent hydrogen, halogen having an atomic number less than 53 or nitro group, $X_3$ represents hydrogen or halogen having an atomic number less than 53, $X_4$ represents hydrogen or iodine, and $X_5$ represents hydrogen, nitro group, chlorine or methyl group.

Said compounds have lower antifungal and bactericidal activity than that of the halo-salicylanilide provided in the instant invention.

SUMMARY OF THE INVENTION

An object of the present invention is to provide a new halo-salicylanilide having high antifungal and bactericidal activity.

Briefly said object of the present invention can be attained by a halo-salicylanilide of the following formula

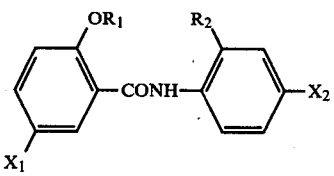

wherein $R_1$ represents hydrogen or acyl group, $R_2$ represents alkyl group, and both $X_1$ and $X_2$ represent halogen.

BRIEF DESCRIPTION OF THE PHOTOGRAPH

DETAILED DESCRIPTION OF THE PREFERRED EMBODIMENTS

Figure 1:
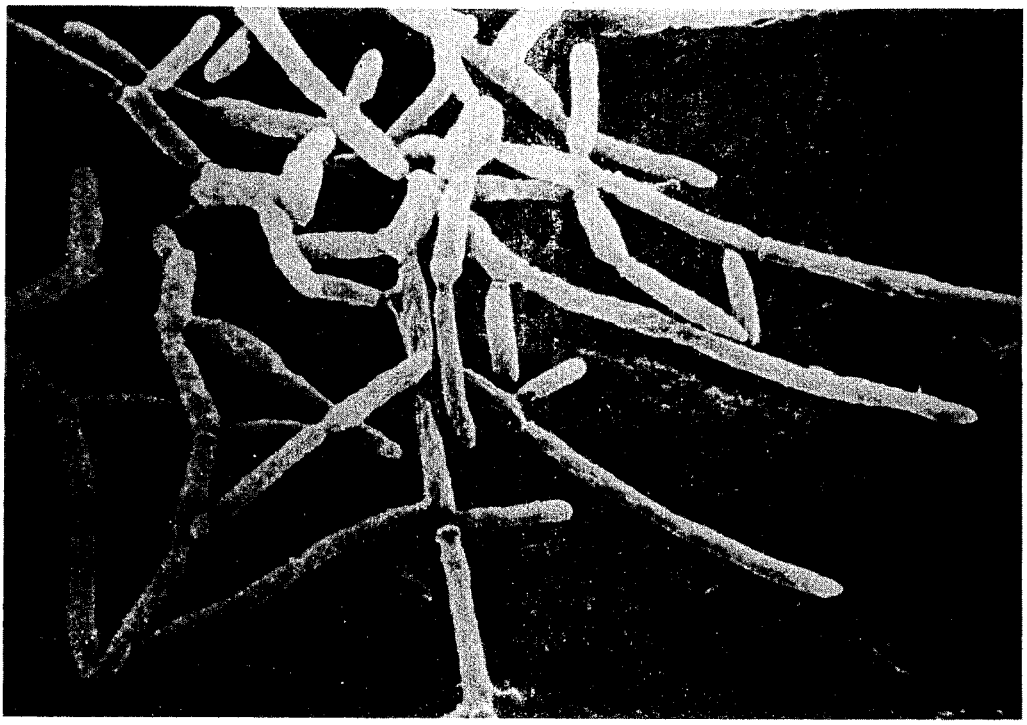
FIG. 1 shows a photograph of the scanning electron microscope showing the multiplying state of *Candida albicans* ATCC 10259 which is first cultured in a culture medium containing the compound of Contrast 2 then removed and cultured in a culture medium without said compound.

A halo-salicylanilide provided in the instant invention has the following formula

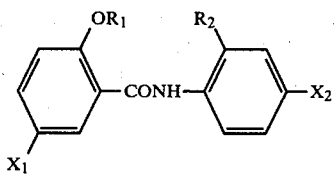

wherein $R_1$ represents hydrogen or acyl group, $R_2$ represents alkyl group, and both $X_1$ and $X_2$ represent halogen, and is characterized by alkyl group which substitutes position 2' of halo-salicylanilide. All halo-salicylanilides in the prior arts did not substitute by said alkyl group in position 2'. Therefore said halo-salicylanilide provided in the instant invention is a novel compound. Said alkyl group is desirably lower alkyl group having less than 4 carbon atoms.

The halo-salicylanilide provided in the instant invention has extremely higher antifungal and bactericidal activity than that of the halo-salicylanilides in the prior arts, and further more, it is worthy of special mention that the halo-salicylanilide provided in the instant invention obstructs fungi or bacteria to possess the resistance for said compound and acts dynamically on fungi or bacteria to obstruct protein synthesis in fungi or bacteria while the halo-salicylanilides in the prior arts have no ability to obstruct fungi or bacteria to possess the resistance for the compounds and act only statically on fungi or bacteria.

Thus mechanism of antifungal and bactericidal activity of said halo-salicylanilide quite differ from that of the halo-salicylanilide in the prior arts.

The halo-salicylanilide provided in the instant invention for instance is produced by following methods.

(1) Halogen substitution of benzene rings of 2'-alkylsalicylanile 5-and 4'-position of 2'-alkylsalicylanilide is substituted by halogen. In said substitution, it has been found that 5 position of 2'-alkylsalicylanilide is first substituted by halogen than 4'-position of said compound is substitutes by halogen.

(2) Condensation reaction between 5-halogenosalicylic ester and 4-halogeno-2-alkyl aniline The halo-salicylanilide provided in the instant invention is obtained by condensation reaction between 5-halogeno-salicylic ester, preferably, 5-halogenosalicylic phenyl ester and 4-halogeno-2-alkyl aniline.

(3) Condensation reaction between 5-halogenosalicyl anilide and 1-halogeno-2-alkyl benzene 5-halogeno-salicylamide is condensed with 1-halogeno-2-alkyl aniline to obtain 5-halogeno-2'-alkyl salycylanilide then 4'-position of said salicylanilide is substituted by halogen.

(4) Condensation reaction between 5-halogeno salicylic chloride and 2-alkyl aniline 5-halogeno salicylic chloride is condensed with 2-alkyl aniline to obtain 5-halogeno-2'-alkyl salicylanilide then 4'-position of said salicyl anilide is substituted by halogen.

(5) Condensation reaction between 5-halogeno salicylic acid and 4-halogeno-2-alkyl aniline This method seems to be one of the most preferable methods. In this method, the halo-salicylanilide is obtained by the condensation reaction between 5-halogeno salicylic acid and 4-halogeno-2-alkyl aniline without the existence of solvent by employing thionyl chloride as a condensation agent preferably under existence of tertiary amine such as pyridine, N-dimethyl aniline and the like. As above mentioned, said condensation reaction is carried out without the existence of solvent but benzene, toluene, paraffine and the like can be also employed as solvents in said reaction. Although phosphorus trichloride and phosphorus pentachloride can be also employed as the condensation agents, higher yield is obtained in case that thionyl chloride is employed as the condensation agents.

Above mentioned five methods are typical but other methods too numerous to mention are also suitable to obtain the halo-salicylanilide provided in the instant invention.

Methyl-group is available as alkyl-group substituting 2'-position of the halo-salicylanilide from the economical viewpoint.

EXAMPLE 1

135 g. of 2'-methyl-4'-chlorosalicylanilide is dissolved in 2,500 cc. of carbon disulfide with heating. Said solution is then rapidly cooled to form a finely dispersed suspension of 2'-methyl-4'-chlorosalicylanilide. A solution of 80 cc. of bromine in 250 cc. of carbon disulfide is added, drop by drop, at room temperature to said suspension with agitation. Said reaction mixture is allowed to stand over night. Thereby 210 g. of 5-bromo-2'-methyl-4'-chloro salicylanilide are obtained. Resulting compound (compound No. 1) forms colorless prism-shaped crystals having properties shown in Table 1 by recrystallizing from ethyl acetate.

TABLE 1

| Melting Point (°C.) | | 238 ~ 239 |
|---|---|---|
| Elementary Analysis Value | C | 49.12 |
| | H | 3.35 |
| | N | 4.21 |
| Mass Spectrum (m/l) | | 339 (M$^+$) |

EXAMPLE 2

6.9 g. of 5-chloro salicylic acid and 7.5 g. of 2-methyl-4-bromoaniline are molten together and said molten mass is pulverized after cooling. 8 g. of phosphorus trichloride are mixed to said powder and said mixture is slowly heated under reflux to 150°–170° C. After said reaction is completed, an excess of phosphorus trichloride is distilled off in a vacuum. Colorless needle-shaped crystals having properties shown in Table 2 of 5-chloro-2'-methyl-4'-bromo salicyl anilide (compound No. 2) is obtained by recrystallizing from ethanol.

TABLE 2

| Melting Point (°C.) | | 209 ~ 213 |
|---|---|---|
| Elementary Analysis Value | C | 49.44 |
| | H | 3.18 |
| | N | 4.06 |
| Mass Spectrum (m/l) | | 339 (M$^+$) |

EXAMPLE 3

45.4 g. of 2'-methyl salicylanilide are dissolved in about 170.0 g. of glacial acetic acid. A solution 50.8 g. of iodine in 20 g. of glacial acetic acid is added, drop by drop, to said solution with agitation and moderately cooling. After said reaction is completed, 70.6 g. of 5-iodo-2'-methyl salicylanilide are obtained by filtration. Said compound is dissolved in 500 cc. of glacial acetic acid and 150 g. of ethyl acetate. 7.0 g. of chlorine are introduced into said solution under existence of a little amount of iron powder at about 40° C. to obtain 5-iodo-2'-methyl-4'-chloro salicylanilide. Resulting compound (compound No. 3) forms slightly yellowish powder having properties shown in Table 3 by recrystallizing from ethyl acetate.

TABLE 3

| Melting Point (°C.) | | 209 ~ 213 |
|---|---|---|
| Elementary | C | 43.42 |
| Analysis Value | H | 281 |
| | N | 3.58 |
| Mass Spectrum (m/l) | | 387 (M+) |

EXAMPLE 4

5.8 g. of 5-chloro acetylsalicylic phenyl ester are heated with 14.2 g. of 2'-methyl-4-chloro aniline and 7.5 g. of 5-methyl naphthalene. The phenol split off thereby is continuously distilled off together with 1-methyl naphthalene. The residue is again mixed with 1-methyl naphthalene then active carbon is added to said mixture and said mixture is heated and filtered. On cooling, 5-chloro-2'-methyl-4' chloro-acetyl salcylanilide is obtained. Resulting compound (compound No. 4) forms colorless needle-shaped crystals having properties shown in Table 4 by recrystallizing from benzene.

TABLE 4

| Melting Point (°C.) | | 190 ~ 192 |
|---|---|---|
| Elementary | C | 57.21 |
| Analysis Value | H | 3.76 |
| | N | 4.04 |
| Mass Spectrum (m/l) | | 337(M+) 295(M+—COCH2) |

EXAMPLE 5

37.1 g. of 5-iodo salicylamide, 43.6 g. of 2-methyl benzene, 10 g. of anhydrous sodium acetate, 1 g. of copper bronze are mixed together and heated under reflux for 4 hours. The molten mass obtained is dissolved in alcohol. Said solution is filtered and concentrated by evaporation. 5-iodo-2'-methyl salicylanilide is obtained thereby. Said compound is then dissolved in about 5 times its amount by weight of a mixture of glacial acetic acid and ethyl acetate (1:1). A solution of 40.8 g. of bromine in 30 cc. of glacial acetic acid is added to said solution to obtain 5-iodo-2'-methyl-4'-bromo salicylanilide. Resulting compound (compound No. 5) forms colorless needle-shaped crystals having properties shown in Table 5 by recrystallizing from ethanol.

TABLE 5

| Melting Point (°C.) | | 223 ~ 226 |
|---|---|---|
| Elementary | C | 38.95 |
| Analysis Value | H | 2.51 |
| | C | 3.23 |
| Mass Spectrum (m/l) | | 431 (M+) |

EXAMPLE 6

21.4 g. of 5-iodo acetyl salicylic acid, 11.2 g. of 2-ethyl-4-chloro aniline and 15 g. of pyridine are dissolved in 30 cc. of dried benzene. 8 cc. of thionyl chloride is added, drop by drop, to said solution while cooling at 10°–20° C. and agitating. After said reaction is completed, solvent and other volatile substances are disttiled off by heating in a vacuum. The resulting residue is dissolved in aqueous hydro chloride and unreacted starting materials are removed by adding sodium bicarbonate then 5-iodo-2'-ethyl-4'-chloro salicylanilide (compound No. 6) having properties shown in Table 6 is obtained by recrystallizing from benzene.

TABLE 6

| Melting Point (°C.) | | 216 ~ 217 |
|---|---|---|
| Elementary | C | 44.70 |
| Analysis Value | H | 3.31 |
| | N | 3.56 |
| Mass Spectrum (m/l) | | 401 (M+) |

Following halo-salicylanilides shown in Table 7 are obtained by employing methods shown in above mentioned Examples.

TABLE 7

| No | Compound | Melting Point (°C.) | Mass Spectrum (m/l) |
|---|---|---|---|
| 7 | 5-chloro-2'-methyl-4'-bromo chloro salicylanilide | 251 ~ 252 | 295(M+) |
| 8 | 5-chloro-2'-methyl-4'-bromo acetylsalicylanilide | 179 ~ 182 | 381(M+) 339(M+—COCH2) |
| 9 | 5-bromo-2'-methyl-4'-chloro acetylsalicylanilide | 180 ~ 182 | 381(M+) 339(M+—COCH2) |
| 10 | 5-bromo-2'-methyl-4'-bromo salicylanilide | 219 | |
| 11 | 5-bromo-2'-methyl-4'-acetylsalicylanilide | 198 ~ 200 | 425(M+) 383(M+—COCH2) |
| 12 | 5-iodo-2'-methyl-4'-chloro acetylsalicylanilide | 178 ~ 180 | 387(M+—COCH2) |
| 13 | 5-iodo-2'-methyl-4'-bromo acetylsalicylanilide | 205 ~ 209 | 473(M+) 431(M+—COCH2) |
| 14 | 5-fluoro-2'-methyl-4'-chloro salicylanilide | 210 ~ 211 | 279(M+) |
| 15 | 5-fluoro-2'-methyl-4'-chloro acetylsalicylanilide | 171 ~ 172 | 321(M+) |
| 16 | 5-fluoro-2'-methyl-4'-bromo salicylanilide | 225 ~ 226 | 323(M+) |
| 17 | 5-fluoro-2'-methyl-4'-bromo acetylsalicylanilide | 179 ~ 180 | 365(M+) 323(M+—COCH2) |
| 18 | 5-fluoro-2'-methyl-4'-iodo salicylanilide | 246 ~ 248 | 371(M+) |
| 19 | 5-fluoro-2'-methyl-4'-iodo acetylsalicylanilide | 172 ~ 175 | 413(M+) |

In order to test antifungal and bactericidal activity of halo-salicylanilide obtained in above mentioned Examples, following bacteria and fungi are employed.

No. 1 *Escherichia coli* NIHJ JC-2
No. 2 *Pseudomonas aeruqinosa* NC-5
No. 3 *Staphylococcus aureus* FDA-209-P
No. 4 *Bacillus subtilis* PCI-219
No. 5 *Candida albicans* ATCC 10259
No. 6 *Aspergillus flavus* IFO 8558
No. 7 *Trichophyton rubrum* IFO 9185

Bacteria No. 1 to No. 4 are respectively cultured in Hart Infusion bouillon medium at 37° C. for 20 hours and resulting medium liquids are employed for said test. Fungi No. 5 to No. 7 are respectively cultured in Sabouraud agar medium and $10^6$ cell/ml of cell dispersing liquids obtained from said medium are employed for said test.

MIC (Minimum Inhibitory Concentration) of the compounds are respectively obtained by the observation of the multiplying state of cultured in agar medium containing a fixed concentration of the compounds at 37° C. for 4 hours and fungi cultured in Sabouraud agar medium containing a fixed concentration of the compounds at 20° C. for 14 days.

Resulting MIC are shown in Table 8.

TABLE 8

| Compound No. | Sort of Bacterium or Fungus | | | | | | |
|---|---|---|---|---|---|---|---|
| | 1 | 2 | 3 | 4 | 5 | 6 | 7 |
| 1 | >100 | >100 | 0.8 | 0.8 | 50 | 50 | 50 |
| 2 | >100 | >100 | 0.8 | 0.8 | 50 | 50 | 50 |
| 3 | >100 | 10~100 | 0.75 | 1.5 | 6.3 | 6.3 | 6.3 |
| 4 | >100 | >100 | 0.1 | 0.2 | 100 | — | 0.2 |
| 5 | >100 | 10~100 | 0.37 | 0.75 | 3.2 | 3.2 | 3.2 |
| 6 | >100 | 10~100 | 0.75 | 0.75 | 6.3 | 3.2 | 3.2 |
| 7 | >100 | >100 | 0.8 | 0.8 | 100 | — | 25 |
| 8 | >100 | >100 | 0.8 | 0.8 | 100 | — | <0.8 |
| 9 | >100 | >100 | 0.8 | 0.8 | 100 | — | 25 |
| 10 | >100 | >100 | 0.2 | 0.4 | 100 | — | 0.8 |
| 11 | >100 | >100 | 0.2 | 0.4 | 100 | — | 0.8 |
| 12 | >100 | 100 | 0.8 | 0.8 | 100 | — | 0.8 |
| 13 | >100 | 100 | 0.2 | 0.4 | 100 | — | 12.5 |
| 14 | >100 | 100 | 0.4 | 0.4 | 100 | — | <0.8 |
| 15 | >100 | 100 | 0.4 | 0.4 | 100 | — | <0.8 |
| 16 | >100 | 100 | 0.4 | 0.4 | 100 | — | <0.8 |
| 17 | >100 | 100 | 0.4 | 0.4 | 100 | — | <0.8 |
| 18 | >100 | 100 | 0.4 | 0.4 | 100 | — | <0.8 |
| 19 | >100 | 100 | 0.4 | 0.4 | 100 | — | <0.8 |
| Contrast No. | | | | | | | |
| 1 | >100 | >100 | 10~100 | 10~100 | >100 | >100 | 50 |
| 2 | >100 | >100 | 10~100 | 10~100 | 50 | >100 | 50 |
| 3 | >100 | 10~100 | >100 | >100 | 10~100 | 50 | 50 |
| 4 | >100 | 10~100 | >100 | >100 | 10~100 | 25 | 25 |

In Table 8, contrast No. 1 is a halo-salicylanilide of the following formula

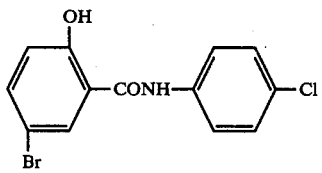

2'-position of said halo-salicylanilide is not substituted by alkyl group and said halo-salicylanilide is disclosed in U.S. Pat. No. 2,802,029, contrast No. 2 is a halo-salicylanilide of the following formula

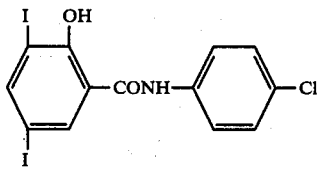

2'-position of said halo-salicylanilide is also not substituted by alkyl group while 3-position of said compound is substituted by iodine and said halo-salicylanilide is disclosed in French Pat. No. 2,162,454, contrast No. 3 is undecylenic acid which is commercial antifungal and bactericidal chemicals, and contrast No. 4 is griseofulvin which is also commercial chemicals.

Referring now to Table 8, in said Examples the halo-salicylanilides provided have respectively remarkable higher antifungal and bactericidal activity than that of the contrasts proposed and said halo-salicylanilides are especially effective on bacteria No. 3 and No. 4, and fungi No. 5, No. 6 and No. 7. This testifies that alkyl group of 2'-position of the halo-salicylanilides is significant for the activities of the compound. In the halo-salicylanilides, compounds No. 3, No. 5, No. 6, No. 13 and No. 14 to No. 19 especially have remarkable antifungal and bactericidal activity. This shows that the halo-salicylanilides have most effective activity in case that $X_1$ of 5-position of the halo-salicylanilides is iodine or fluorine. Especially the halo-salicylanilides having fluorine in 5-position are very useful for agricultural medicines.

Figure 2:
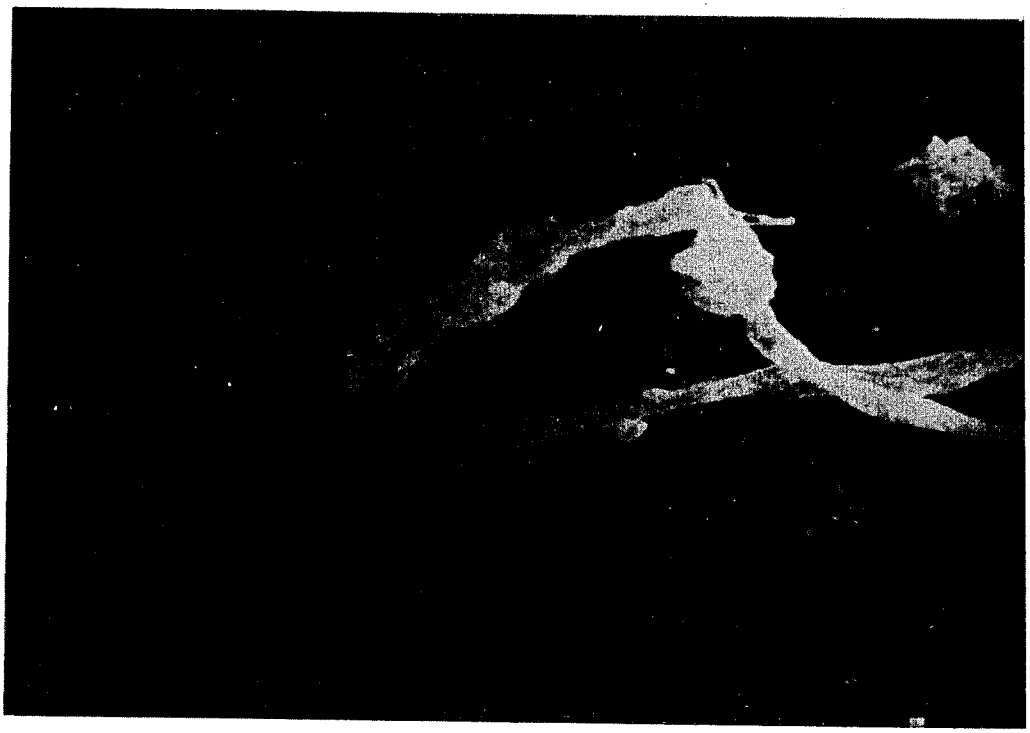
FIG. 2 shows a photograph of the scanning electron microscope showing the multiplying state of *Candida albicans* ATCC 10259 which is first cultured in a culture medium containing the halo-salicylanilide of Example 3 then removed and cultured in a culture medium without said halo-salicylanilide.

Photograph shown in FIG. 1 shows the multiplying state of Candida albicans ATCC 10259 which is first cultured in a culture medium containing the compound of Contrast No. 2 then removed and cultured in a culture medium without said compound, and Photograph shown in FIG. 2 shows the multiplying state of said fungi which is first cultured in a culture medium containing the compound No. 3 then removed and cultured in a culture medium without said compound.

Referring FIG. 1 and FIG. 2, the fungi again starts to multiply after it is removed in the culture medium without the compound of Contrast No. 2 while the fungi does not start to multiply even after it is removed in the culture medium without compound No. 3 and the destruction of the cell membranes of the fungi is observed.

Although the halo-salicylanilides provided in the instant invention is the halogen substitutions of 2'-alkyl-salicylanilide in 5 and 4'-position, the halo-salicylanilides substituted by halogen, alkyl-group, nitro-group and the like in other positions are available in the instant invention.

We claim:
1. A halo-salicylanilide of the following formula

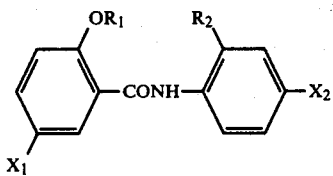

wherein $R_1$ represents hydrogen or an acyl group, $R_2$ represents an alkyl group, $X_1$ represents fluorine, chlorine, or iodine, and $X_2$ represents fluorine, chlorine, bromine or iodine when $X_1$ is fluorine or iodine, $X_2$ represents fluorine, bromine or iodine when $X_1$ is chlorine and $R_1$ is hydrogen, and $X_2$ represents fluorine, chlorine, bromine or iodine when $X_1$ is chlorine and $R_1$ is an acyl group.

2. The halo-salicylanilide of claim 1, wherein $R_2$ is a methyl group.

3. The halo-salicylanilide of claim 1, wherein $X_1$ is iodine.

4. The halo-salicylanilide of claim 1, wherein $X_1$ is fluorine.

5. The halo-salicylanilide of claim 2, wherein $X_1$ is iodine.

6. The halo-salicylanilide of claim 2, wherein $X_1$ is fluorine.

* * * * *